United States Patent [19]

Rosencwaig

[11] 4,028,932

[45] June 14, 1977

[54] PHOTO ACOUSTIC CELL

[75] Inventor: Allan Rosencwaig, Summit, N.J.

[73] Assignee: Hoffman-La Roche Inc., Nutley, N.J.

[22] Filed: Apr. 14, 1975

[21] Appl. No.: 567,640

Related U.S. Application Data

[63] Continuation-in-part of Ser. No. 370,526, June 17, 1973, Pat. No. 3,948,345.

[52] U.S. Cl. .................................. 73/67.2; 73/24
[51] Int. Cl.² .................................. G01N 21/24
[58] Field of Search .......... 73/67.2, 24; 250/216, 250/493, 343, 345, 347; 181/142; 331/94.5 R, DIG. 1

[56] References Cited

UNITED STATES PATENTS

| | | | |
|---|---|---|---|
| 3,532,181 | 10/1970 | DeMaria et al. | 250/216 |
| 3,583,212 | 6/1971 | Nanney et al. | 73/67.2 |
| 3,700,890 | 10/1972 | Kreuzer | 250/343 |
| 3,820,901 | 6/1974 | Kreuzer | 356/97 |

OTHER PUBLICATIONS

Bell, A. G. *Upon the Production of Sound by Radiant Energy*, in Philosophical Magazine, vol. 11, pp. 510–528, 1881.

Kreuzer et al., *Nitric Oxide Air Pollution: Detection by Optoacoustic Spectroscopy*, Science, vol. 173, pp. 45–47, July 1971.

Kreuzer et al., *Air Pollution: Sensitive Detection of Ten Pollutant Gases by Carbon Monoxide Lasers*, Science, vol. 177, pp. 347–349, July 28, 1972.

*Primary Examiner*—Richard C. Queisser
*Assistant Examiner*—Stephen A. Kreitman
*Attorney, Agent, or Firm*—Samuel L. Welt

[57] ABSTRACT

Three embodiments of an improved photo acoustic cell for use in analyzing solid and quasi-solid samples are disclosed. Each cell includes a sample holding chamber having one wall or portion of one wall thereof made from a light transparent material. The sample holding chamber in each embodiment is connected to a microphone by a thin tube which renders the cell, which includes the chamber tube and microphone, an acoustical resonant structure at a frequency within the response characteristics of the microphone. In one embodiment, means are disclosed for pressuring the inside of the cell as well as equalizing the pressure on the outside of the tube. In a second embodiment, the sample to be analyzed forms a portion of the cavity walls and means are provided for reducing the pressure in the cavity to hold the sample securely to the remaining structure for defining the cavity. In this embodiment a fiber optic element brings the light into the chamber. In the third embodiment the cell is mounted relative to a support structure so that different portions of the sample can be brought into relationship with can advantageously be employed to analyze plates, paper or the like which result from chromatographic techniques.

25 Claims, 4 Drawing Figures

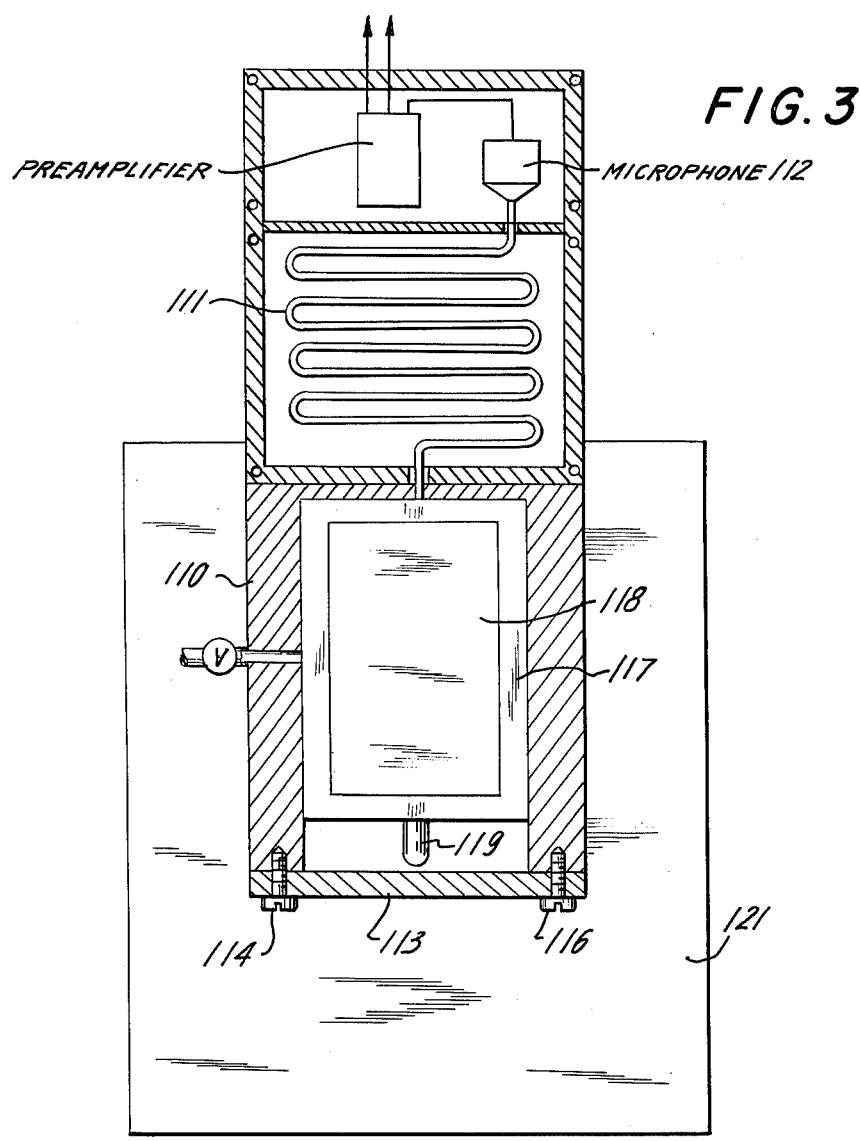
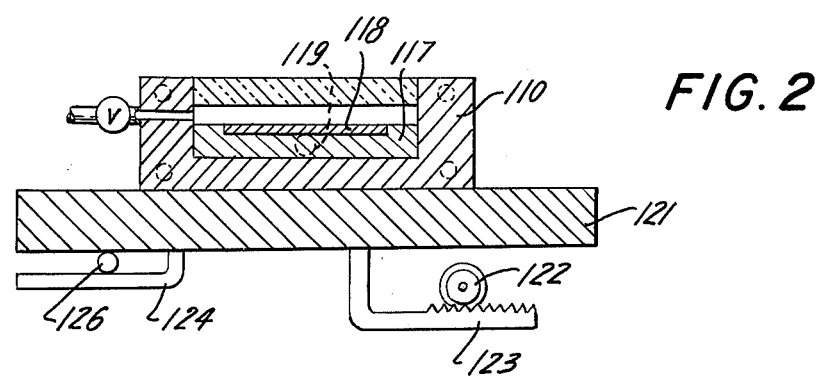

PHOTO ACOUSTIC CELL

CROSS-REFERENCE

This is a continuation-in-part of my copending Pat. application Ser. No. 370,526 filed June 17, 1973, now U.S. Pat. No. 3,948,345.

FIELD OF THE INVENTION

This invention relates to photo-acoustic cells and, particularly, to photo-acoustic cells for analyzing solid or quasi-solid samples.

BACKGROUND OF THE INVENTION

An article appeared on page 510, volume 11, of the Philosophical Magazine in 1881 in which Alexander Graham Bell reported upon certain experiments which he conducted to study the sound-emitting properties of materials when exposed to the action of rapidly interrupted sunlight. Bell, among other things, introduced samples of material into a chamber and passed an intermittent beam of sunlight therein to produce audible effects. Bell observed that when the sample was in an acoustical resonant chamber the maximum response was achieved at a frequency of interruption equivalent to the resonant frequency of the chamber. While Bell was primarily interested in producing sound, he did recognize that this effect could be employed to study the properties of the material.

In my copending patent application, referred to above, I disclosed a method and apparatus for analyzing substances which employed the photo-acoustic phenomenon first recognized by Bell but apparently not developed by others thereafter.

In the devices discussed by Bell, and in my previous devices, the sample to be analyzed (or which was to respond to the light) was included in a chamber which was made sufficiently long to be resonant at the frequency of interest. Upon further study of the photo-acoustic phenomenon, I have discovered that substantially greater signals can be obtained by limiting the volume of fluid in the cell and that limitation of such volume can most optimally be obtained by designing the sample holding chamber and the remainder of the device forming the resonant structure to optimize the overall cell volume.

I have also found that further improvement of the signal response can be achieved as shall be discussed below.

I have also realized that the new cell structure which results from the above-mentioned discoveries enable the photo-acoustic effect to be employed in chromatography as well as direct analysis of samples such as skin with an open-ended cell.

Therefore, it is an object of this invention to provide improved photo-acoustic cells.

It is a further object of this invention to produce improved photo-acoustic cells with increased signal response.

It is still a further object of this invention to provide improved photo-acoustic cells which can be applied to a wide variety to uses.

BRIEF DESCRIPTION OF THE INVENTION

With these and other objects in view the present invention contemplates an apparatus for use in analyzing a solid or quasi-solid sample which includes portions thereof for defining a sample chamber to hold the sample to be analyzed. The portion defining the sample chamber passes light through a part thereof. The sample chamber defined has a predetermined volume. A device is also included which is responsive to pressure variations in a fluid and structure is provided for fluidly connecting the sample chamber to the pressure variation responsive device. The volume of the connecting device has a predetermined relationship to the predetermined volume.

In the preferred embodiment, the connecting device is a tube which renders the apparatus an acoustic resonant structure having a fundamental frequency between 100 and 1,000 hertz.

While there are various ranges of relationship between the volume of the sample chamber and the volume of the connecting means, it has been found that optimum results can be achieved when the two volumes are substantially equal. It has been also found that the predetermined volume should be between 1 and 50 cubic centimeters.

In one embodiment of this invention, the sample forms a part of the sample chamber while in another embodiment the sample chamber is mounted for movement relative to a support structure.

DESCRIPTION OF THE DRAWINGS

For a more complete understanding of this invention reference should be made to the following detailed description and drawings in which:

FIG. 2 is a bottom-sectional view of a second embodiment of a photo-acoustic cell embodying the principles of this invention;

FIG. 3 is a plan-sectional view partially in block diagram form showing the embodiment of FIG. 2.

DETAILED DESCRIPTION OF THE INVENTION

Figure 1:
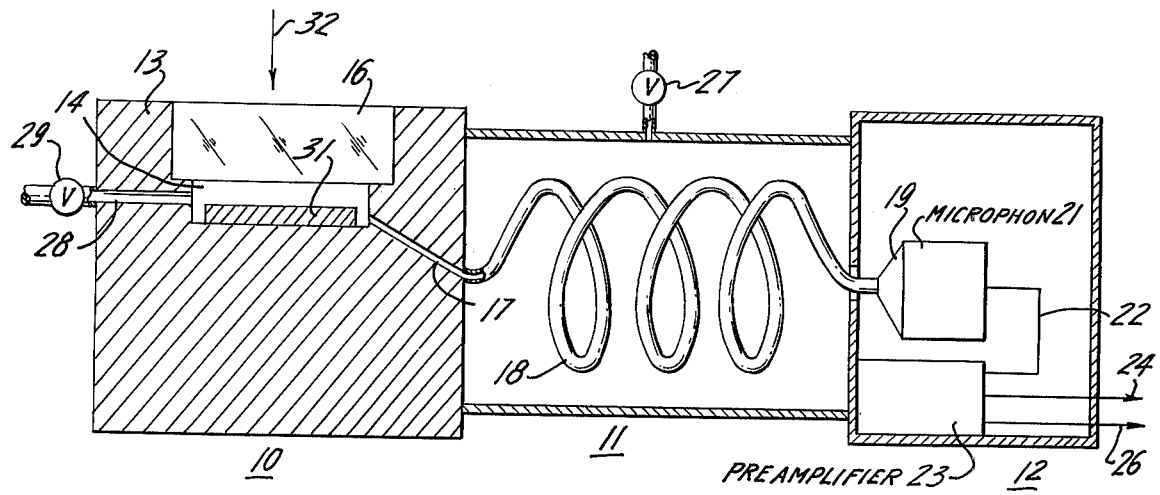
FIG. 1 is a drawing partially in section and partially in block diagram form showing a photo-acoustic cell embodying the principles of this invention.

Referring now to FIG. 1, we see a photo-acoustic cell embodying the principles of this invention. The cell includes three basic portions. The first portion is a sample chamber defining portion 10, the second portion is a connection portion 11, while the third portion is a pick-up portion 12. The cell of FIG. 1, as the other cells disclosed herein, may be employed in systems such as the one disclosed in the above-referred-to parent application hereof.

The sample chamber defining portion 10 includes an aluminum or stainless steel block 13 having a sample chamber 14 covered by a window 16 which passes light but is opaque to sound. A channel 17 connects the chamber 14 to a plastic tube 18 which is also connected through a funnel 19 to a microphone 21. The microphone 21 is connected by a lead 22 to a preamplifier 23 which is, in turn, connected by leads 24 and 26 to appropriate detection circuitry. The tube 18 is contained in the portion 11. The portion 11 may be pressurized by application of fluid under pressure through valve 27. The chamber 14 is also connected via channel 28 to a valve 29 through which fluid under pressure can be applied to the sample chamber 14 and therefore the inside of tube 18. It should be noted that the valve 29 is connected to the interior of the sample chamber 14 and thus the interior of the tube 18 while the valve 27 would provide fluid to the exterior of the tube 18. The tube 18 may be made of a plastic material and the need for pressure balancing would thus be advantageous. FIG. 1 shows, also, a sample 31 to be analyzed.

In operation, a chopped beam of light 32 (from a source not shown) is projected through the window 16 onto the sample 31. If the sample 31 absorbs light at the wavelength of the light 32, the sample 31 is raised to a higher energy state. In most cases the absorbed energy is dissipated as heat. Since the application of the light is periodic, a periodic heat flow occurs from the sample 31 to the surrounding fluid (in this case gas). The periodic heat flow to the gas produces periodic heating of the gas which, in turn, produces periodic pressure changes in the fluid inside the chamber 14, tube 18, funnel 19, and impinging upon a microphone 21. As discussed in the parent application, the length of the fluid path discussed above is optimized at approximately one half the wavelength of the chopped frequency of the light 32 so that an acoustical resonant structure results. In this way, the pressure signal provided to the microphone 21 is increased by the Q of the resonant structure.

It has been found that the strength of the signal incident upon the microphone 21 increases linearly with the power of the light beam 32, the ratio of the specific heats ($C_p/C_v$) of the gas within the cell and the equilibrium pressure within the cell. It has also been found that the strength of the signal incident upon the microphone 21 is inversely proportional to the volume of gas within the cell and the frequency at which the light 32 is chopped. Since the strength of the signal incident upon the microphone 21 is inversely proportional to the volume of gas within the cell, it would seem that the optimum cell would have a sample chamber 14 of a minimum size to accommodate the sample 31 and a narrow tube 18. In fact, one would initially think that the tube 18 should be as narrow as possible in order to add as little volume within the cell as possible and still maintain the resonant length to provide the increased signal based upon the Q thereof.

It has also been found, however, that as the inside diameter of the tube 18 is decreased, viscous damping effects come into play. Since viscous damping increases as the frequency decreases, there is a range of frequencies and volume which will produce optimum results. For a better understanding of viscous damping of sound waves in cylindrical tubes, see "The Theory of the Propagation of Plane Sound Waves in Tubes" by D. E. Weston which appeared in volume B66, page 695, of the Proceedings of the Physical Society (London 1953).

From the above, it can be seen that optimally the volume of gas in the passageway 17, tube 18 and funnel 19 should be approximately equal to the volume of gas in the chamber 14 (and passageway 28). As the volume of gas in the passageway 17, tube 18 and funnel 19 increases above the volume in the chamber, signal strength is lost. However, since viscous damping effects at a constant frequency are decreased as the size of the tube 18 is increased, the overall Q of the system is increased with a larger tube which would increase signal strength. Further, if the frequency is lowered as the size of the tube 18 is increased, the strength of the signal will be increased because of the lowering of the frequency. Therefore, optimum photo-acoustic cells can be designed with the volume of gas in the passageway 17, tube 18 and funnel 19 up to ten times the volume of gas in the sample chamber 14.

It is, however, preferable to keep the volume of gas in the passageway 17, tube 18 and funnel 19 within a range of two times to one half the volume of gas in the sample chamber 14 and adjust the frequency to the optimum value. By using the range of two to one half times the volume of gas in the passageway 17, tube 18, and funnel 19 a signal strength is not altered by more than a factor of two. If the volume of gas in the passageway 17, tube 18 and funnel 19 were less than one half times the volume of gas in the sample chamber 14, viscous damping effects would begin the predominate as the frequency were lowered to take advantage of the increased strength from the lower frequencies.

It has been found that a sample chamber volume should be greater than one cubic centimeter to accommodate the sample to be analyzed. However, the sample chamber should have a volume of no greater than 50 cubic centimeters or else signal strength will be unduly limited.

It has been found that optimum cells can be designed having tube 18 with a radius between 0.01 and 0.10 centimeters thereby providing a passageway having a clearance between 0.02 and 0.20 centimeters. It has also been found that chopping frequencies of between 100 and 1,000 hertz are optimum. To this end the resonant frequency of the photo-acoustic cell should be in that range and the light 32 should be chopped at the fundamental frequency of the resonant structure.

If it is desired to increase the signal strength a source of pressurized gas can be applied through valve 29. If a flexible tube is used for the tube 18, a counterpressure can be applied through the valve 27 to maintain the physical properties of the tube 18.

When gas other than air is employed in the photo-acoustic cell, one can select a gas having a specific heat ($C_p/C_v$) greater than air. However, it is contemplated that in most instances air at 1 atmosphere will be employed in the photo-acoustic cell.

Referring now to FIGS. 2 and 3, we see a photo-acoustic cell in accordance with the teachings of this invention mounted for movement with respect to a support structure to perform chromatographic analysis. The cell includes a sample holding portion 110, a connecting portion 111, and a pickup portion 112. The sample holding portion 110 is adapted by end plate 113 and screws 114 and 116 to receive a sample tray 117 having chromatographic paper, plate, or film 118 thereon. The tray 117 has a handle 119 for facilitating entry thereof into the chamber. The cell is slidably mounted on a support table 121 for up and down movement in FIG. 3 which would be in and out of the paper in FIG. 2. The support table 121 is mounted for left and right movement by gear 122 to bracket 123, bracket 124 and support pin 126. In this way the cell of FIGS. 2 and 3 can be moved relative to a fixed light source to analyze materials at particular points on the paper plate or film 118.

Figure 4:
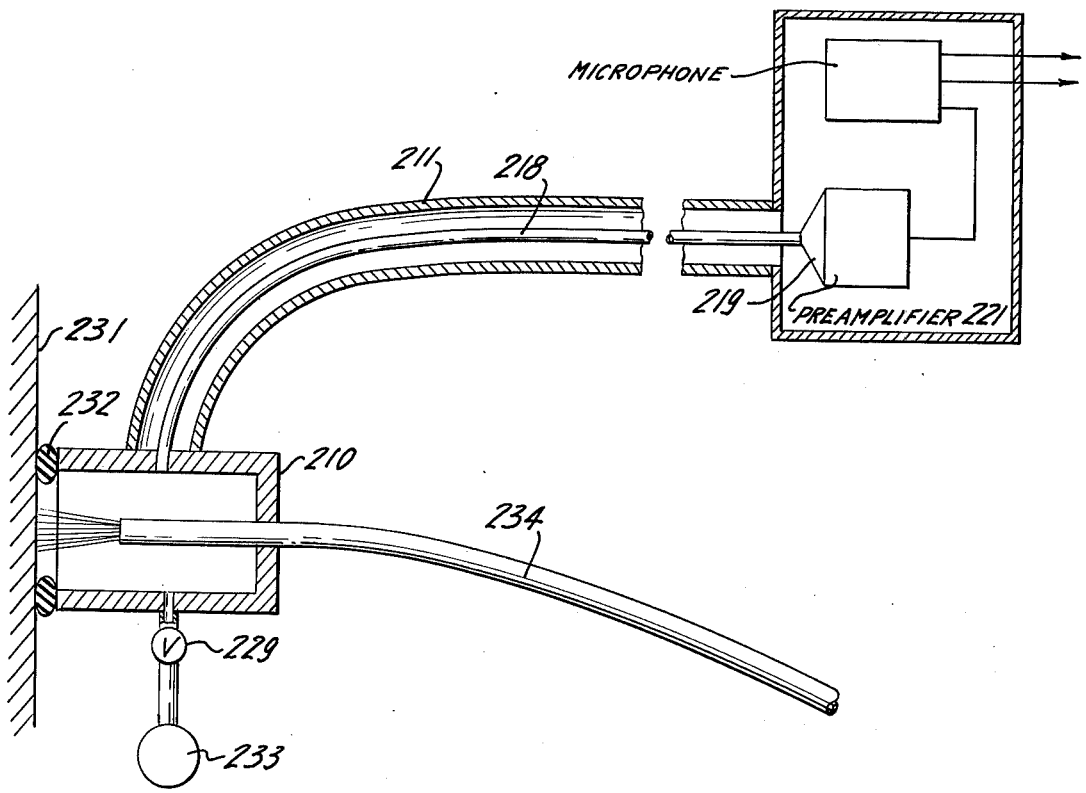
FIG. 4 is a sectional view partially in block diagram form showing a third embodiment of a photo-acoustic cell embodying the principles of this invention.

Referring now to FIG. 4, we see a third embodiment of the photo-acoustic cell embodying the principles of this invention. In this embodiment the chamber is defined by a structure 210 having one side thereof open. That side is closed by the sample 231 which may be the skin of an individual. An O ring or gasket 232 is interposed between the sample 231 and the chamber forming device 210. A valve 229 connects a suction-producing device 233 to produce a partial vacuum therein.

After the partical vacuum is developed, the valve 229 is shut to maintain the same. In this way, the device 210 is held against the skin. Of course it should be understood that a small vacuum is employed so that the signal strength is not materially depreciated. In order to develop a flexible device for measurements on samples such as individuals' skin, a fiber optic element 234, such as a fiber optic bundle, is employed to bring the light to the surface of the sample 231. In a like manner a connecting tube 218 is mounted in a flexible jacket 211 and is connected to the microphone 221 by a funnel 219.

It should be clear that the additional elements in FIGS. 2, 3 and 4 are analogous to those described in detail in FIG. 1. It should also be understood that both of the embodiments shown in FIGS. 2, 3 and 4 operate upon the same principles as described in detail with respect to the embodiment in FIG. 1.

While this invention has been described with respect to three particular embodiments thereof modifications thereof can be made without departing from the spirit or scope hereof.

What is claimed is:

1. An apparatus for use in analyzing a solid or quasi-solid sample including:
    first means for defining a sample chamber to hold said sample to be analyzed and for enclosing a fluid therein; said sample chamber defining means including a portion thereof for passing radiant energy having a periodically varying magnitude; said sample chamber defined having a predetermined volume;
    second means responsive to pressure variations in said fluid for providing an electrical signal;
    third means for fluidly connecting said sample chamber to said second means; said third means having a volume between one half and ten times said predetermined volume; and
    said predetermined volume being between 1 and 50 cubic centimeters.

2. The apparatus as defined in claim 1 in which said third means is a passageway having a clearance between 0.02 and 0.20 centimeters.

3. The apparatus as defined in claim 1 in which said first, second and third means defines an acoustic resonant structure having a fundamental frequency of between 100 and 1,000 hertz.

4. The apparatus as defined in claim 3 in which said third means is a tube having a radius between 0.01 and 0.10 centimeters.

5. The apparatus as defined in claim 1 in which said volume of said third means is between one-half and two times said predetermined volume.

6. The apparatus as defined in claim 1 in which said volume of said third means is substantially equal to said predetermined volume.

7. The apparatus as defined in claim 1 in which said sample forms a part of said sample chamber defining means.

8. The apparatus as defined in claim 7 also including:
    an optical fiber for bringing light to said portion of said first means which passes light.

9. The apparatus as defined in claim 1 also including a support structure; and
    said first means is mounted for movement relative to said support structure.

10. The apparatus as defined in claim 9 in which said third means is a tube having a clearance between 0.02 and 0.20 centimeters.

11. The apparatus as defined in claim 10 in which said first, second and third means define an acoustic resonant structure having a fundamental frequency of between 100 and 1,000 hertz.

12. The apparatus as defined in claim 1 also including:
    means for applying gas under pressure to said sample chamber.

13. The apparatus as defined in claim 12 in which said applied gas has a ratio of specific heats ($C_p/C_v$) greater than air.

14. An apparatus for use in analyzing a solid or quasi-solid sample in which said sample forms a part of said sample chamber defining means including:
    first means for defining a sample chamber to hold said sample to be analyzed and for enclosing a fluid therein; said sample chamber defining means including a portion thereof for passing radiant energy having a periodically varying magnitude; said sample chamber defined having a predetermined volume;
    second means responsive to pressure variations in said fluid for providing an electrical signal;
    third means for fluidly connecting said sample chamber to said second means; said third means having a volume between one half and ten times said predetermined volume; and
    means for maintaining the pressure in said chamber below 1 atmosphere.

15. The apparatus as defined in claim 14 in which said third means is a passageway having a clearance between 0.02 and 0.20 centimeters.

16. The apparatus as defined in claim 15 in which said first, second and third means defines an acoustic resonant structure having a fundamental frequency of between 100 and 1,000 hertz.

17. The apparatus as defined in claim 16 in which said predetermined volume is between 1 and 50 cubic centimeters.

18. The apparatus as defined in claim 14 also including:
    an optical fiber for bringing radiant energy to said portion of said first means which passes radiant energy.

19. An apparatus for analyzing a solid or quasi-solid sample including:
    first means for defining a sample chamber to hold said sample to be analyzed; said sample chamber defining means including a portion thereof for passing radiant energy having a periodically varying magnitude; said sample chamber defined having a predetermined volume;
    said predetermined volume being less than 50 cubic centimeters;
    second means responsive to pressure variations in a fluid for providing an electrical signal; and
    third means for fluidly connecting said sample chamber to said second means; said third means having a volume less than twice said predetermined volume.

20. The apparatus as defined in claim 19 in which said third means is a passageway having a clearance between 0.02 and 0.20 centimeters.

21. The apparatus as defined in claim 20 in which said first, second and third means defines an acoustic resonant structure having a fundamental frequency of between 100 and 1,000 hertz.

22. The apparatus as defined in claim 19 also including a support structure; and
said first means is mounted for movement relative to said support structure.

23. The apparatus as defined in claim 19 also including:
means for applying gas under pressure to said sample chamber.

24. The apparatus as defined in claim 23 in which said applied gas has a ratio of specific heats ($C_p/C_v$) greater than air.

25. The apparatus as defined in claim 19 in which said sample forms a part of said sample chamber defining means.

* * * * *

UNITED STATES PATENT OFFICE
CERTIFICATE OF CORRECTION

Patent No. 4,028,932          Dated June 14, 1977

Inventor(s) Allan Rosencwaig

It is certified that error appears in the above-identified patent and that said Letters Patent are hereby corrected as shown below:

In the Abstract, line 21, after "with" insert -- a light source for sequential analysis. This type of cell --.

Column 6, line 2, change "tube" to -- passageway --.

Figure 1, the word "MICROPHON 21" should read -- MICROPHONE 21 --.

Figure 4, the word "MICROPHONE" should read -- PREAMPLIFIER --.

Figure 4, the word "PREAMPLIFIER 221" should read -- MICROPHONE 221 --.

Signed and Sealed this

Twenty-first Day of February 1978

[SEAL]

Attest:

RUTH C. MASON
Attesting Officer

LUTRELLE F. PARKER
Acting Commissioner of Patents and Trademarks